(12) United States Patent
Joo

(10) Patent No.: US 9,901,712 B2
(45) Date of Patent: Feb. 27, 2018

(54) CATHETER AND MANUFACTURING METHOD THEREOF

(71) Applicant: IMEDICOM, Gunpo-si, Gyeonggi-do (KR)

(72) Inventor: Don-Soo Joo, Gunpo-si (KR)

(73) Assignee: IMEDICOM, Gunpo-si, Gyeonggi-Do (KR)

( * ) Notice: Subject to any disclaimer, the term of this patent is extended or adjusted under 35 U.S.C. 154(b) by 102 days.

(21) Appl. No.: 14/906,044

(22) PCT Filed: Jul. 18, 2014

(86) PCT No.: PCT/KR2014/006542
§ 371 (c)(1),
(2) Date: Jan. 19, 2016

(87) PCT Pub. No.: WO2015/016517
PCT Pub. Date: Feb. 5, 2015

(65) Prior Publication Data
US 2016/0158495 A1    Jun. 9, 2016

(30) Foreign Application Priority Data

Aug. 1, 2013 (KR) .................. 10-2013-0091411
Jan. 7, 2014 (KR) .................. 10-2014-0001809

(51) Int. Cl.
*A61M 31/00* (2006.01)
*A61M 25/01* (2006.01)
*A61M 25/00* (2006.01)

(52) U.S. Cl.
CPC .... *A61M 25/0147* (2013.01); *A61M 25/0009* (2013.01); *A61M 25/0054* (2013.01); *A61M 25/0136* (2013.01); *A61M 2025/015* (2013.01)

(58) Field of Classification Search
CPC .......... A61M 25/0147; A61M 25/0054; A61M 25/0136; A61M 2025/015; A61M 25/0144; A61M 2025/0034
USPC ........................................ 604/95.04
See application file for complete search history.

(56) References Cited

U.S. PATENT DOCUMENTS

| | | | | |
|---|---|---|---|---|
| 6,146,355 A | * | 11/2000 | Biggs | A61M 25/0136 604/95.01 |
| 6,213,974 B1 | * | 4/2001 | Smith | A61M 25/0136 600/139 |
| 2006/0151923 A1 | | 7/2006 | Wilkowske et al. | |
| 2012/0209073 A1 | | 8/2012 | McWeeney et al. | |
| 2013/0030248 A1 | | 1/2013 | Matsumaru | |

FOREIGN PATENT DOCUMENTS

JP    4441490 B2    3/2010

* cited by examiner

*Primary Examiner* — Phillip Gray
(74) *Attorney, Agent, or Firm* — Rabin & Berdo, P.C.

(57) ABSTRACT

A catheter is provided, which includes a tube including a first portion, a second portion connected to the first portion and having a less rigidity than the first portion, and a plurality of holes longitudinally penetrating the first portion and the second portion and being isolated from one another, a wire passing through two of the plurality of holes of the tube, and a cap being engaged with an extrusion portion of the wire extruded from the two holes of the tube in a manner of enclosing the extrusion of the wire, being connected to one end of the tube, and having a greater rigidity than the first portion and the second portion of the tube.

5 Claims, 7 Drawing Sheets

CATHETER AND MANUFACTURING METHOD THEREOF

TECHNICAL FIELD

The present disclosure relates to a catheter and a manufacturing method thereof.

BACKGROUND ART

Catheter is a medical device that can be inserted in a human body and used for a variety of purposes such as injection of medication or rinsing fluids, and so on. Particularly, it is important that an operator can control the catheter to a desired site in the human body with accuracy. To this purpose, U.S. Pat. No. 6,146,355 (Nov. 14, 2000) discloses a catheter of which an end is adjustable from left to right, or from right to left.

FIGS. 6A and 6B illustrate a catheter disclosed in U.S. Pat. No. 6,146,355. FIG. 6A is a top view of the catheter of the above-mentioned patent, and FIG. 6B is a cross sectional view of a lumen extrusion tip 320 of the catheter disclosed in the above-mentioned patent.

According to the US patent mentioned above, the catheter is manufactured by fusing a lumen extrusion shaft 318 of a relatively greater rigidity with a lumen extrusion tip 320 of a relatively less rigidity (see 318A). For reference, FIGS. 6A and 6B correspond to FIGS. 2A and 3C of the above-mentioned US patent, respectively, with the reference numerals in the drawings remain unchanged for convenience.

When using such conventional catheter, an operator rotates an adjustment dial 316 to one direction and pulls the wire 328 to one direction so that the lumen extrusion tip 320 of a relatively less rigidity is bent with respect to the lumen extrusion shaft 318. Accordingly, the catheter can be configured such that an end of the catheter is adjusted to left or right as desired.

Meanwhile, when the operator pulls the wire 328 of the conventional catheter to one direction, as illustrated in FIG. 7, due to tensile force of the wire 328, the lumen extrusion tip 320 of less rigidity is constricted in a diameter direction, resulting in upper and lower lumen openings 318BU, 318BL to deform in shape elliptically. This raises problems such as hindrance to injection of medication (or rinsing fluids), or to insertion of endoscopic device (not illustrated) which is blocked at the lumen openings 318BU, 318BL, rather than being inserted through the lumen openings 318BU, 318BL.

DISCLOSURE OF INVENTION

Technical Problem

An object of the present disclosure is to solve the problems mentioned above, and accordingly, it is an object of the present disclosure to provide a catheter of which an end is kept from deforming even when tensile force is exerted on the wire, and thus can allow efficient injection of medication (or rinsing fluids) or operation of an endoscopic device through the lumen openings.

Further, the objects of the present disclosure are not limited to those mentioned above, but other objects, which are not explicitly mentioned, but can be derived from the configuration of the present disclosure as described below, are also included as the objects of the present disclosure.

Solution to Problem

According to the present disclosure, a catheter is provided, which may include a tube including a first portion, a second portion connected to the first portion and having a less rigidity than the first portion, and a plurality of holes longitudinally penetrating the first portion and the second portion and being isolated from one another, a wire passing through two of the plurality of holes of the tube, and a cap being engaged with an extrusion portion of the wire extruded from the two holes of the tube in a manner of enclosing the extrusion of the wire, being connected to one end of the tube, and having a greater rigidity than the first portion and the second portion of the tube.

According to an embodiment, the cap is injection-molded at the extrusion portion of the wire.

According to an embodiment, pipes, engaged with the wire while surrounding the wire, are respectively fixed to a lower side of the cap to prevent relative sliding of the wire within the cap with respect to the cap when tensile force is exerted on the wire.

According to an embodiment, the respective pipes are engaged with the wire by bonding.

According to an embodiment, the plurality of holes include four holes, among which other two holes except the two holes may be used as medication injection lumens and endoscope insertion lumen, respectively.

According to an embodiment, a manufacturing method of a catheter is provided, which may include disposing the wire within a mold to fabricate the cap, and then fabricating an assembly of the cap and the wire by injection molding, engaging, by bonding, the pipes with the lower side of the cap to surround the wire, and inserting the assembly of the cap and the wire in the tube and then engaging the cap and the tube by bonding.

According to another embodiment, pipes, engaged with the wire while surrounding the wire, are respectively fixed within the cap to prevent relative sliding of the wire within the cap with respect to the cap when tensile force is exerted on the wire.

Further, the pipes may include two pipes.

According to another embodiment, a manufacturing method of a catheter is provided, which may include first assembling the pipes to the wire to prepare the assembly of the wire and the pipes, and disposing the assembly within a mold to fabricate the cap and then engaging the cap and the assembly by injection molding.

Advantageous Effects of Invention

As described above, according to the present disclosure, since the cap with a greater rigidity than the tube is connected to an end of the tube of the catheter, unlike the conventional catheter, the catheter does not suffer a problem of deformed cross section of the tube when the tensile force is exerted on the wire. As a result, it is possible to efficiently inject medication (rinsing fluids), and efficiently insert or adjust an endoscope, through the holes of the tube.

Further, since the pipes are fixedly engaged with the lower side of the cap while surrounding the wire, when the tensile force is exerted on the wire to bend the end of the catheter to a desired direction, the pipes fixedly engaged with the wire are locked in the lower surface of the cap, thus preventing the wire from sliding within the cap with respect to the cap. As a result, the end of the catheter can be bent effectively.

Meanwhile, the effects of the present disclosure are not limited to those described above, but other effects that can

BEST MODE FOR CARRYING OUT THE INVENTION

Figure 1A:
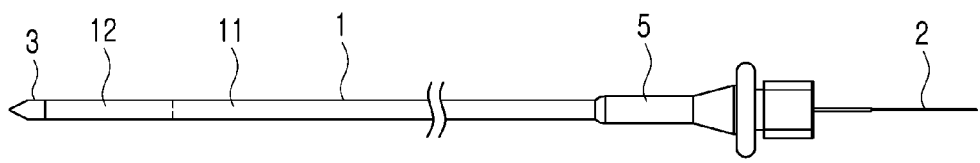
FIGS. 1A and 1B are respectively front view and top view of main configuration of a catheter according to an embodiment of the present disclosure.

Hereinbelow, a catheter according to an embodiment of the present disclosure (simply, 'catheter') will be described with reference to the accompanying drawings. Meanwhile, configurations of the catheter that are irrelevant to the concept of the present disclosure are not described in detail since they would obscure the invention with unnecessary details.

First, as illustrated in FIGS. 1 to 5, the catheter includes a tube 1, a wire 2 and a cap 3. For reference, the tube 1 may be inserted in a manifold 5 and fixed therein. As an adjustment dial (not illustrated), to which both ends of the wire 2 are respectively fixed, is rotated clockwise or counter-clockwise, the tube 1 is bent to a desired direction.

In this example, the tube 1 may include a first portion 11, a second portion 12 connected to the first portion 11 and having a less rigidity (i.e., bending rigidity) than the first portion 11, and a plurality of holes 13, 14, 15, 16 longitudinally penetrating the first portion 11 and the second portion 12 and being isolated from one another. The plurality of holes may include various number of holes, but an embodiment of having four holes will be described below for example. Meanwhile, the holes 13, 14 may be used as smaller-diameter holes through which the wire 2 is inserted, and the holes 15, 16 may be used as larger-diameter holes for the purpose of medication injection and endoscopic insertion.

Figure 3:
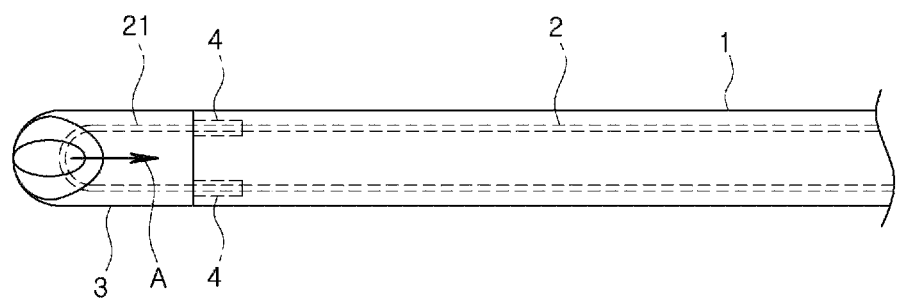
FIG. 3 is a view provided to explain a method of assembling a wire, a cap, and a pipe of the catheter of FIG. 1.
Figure 4:
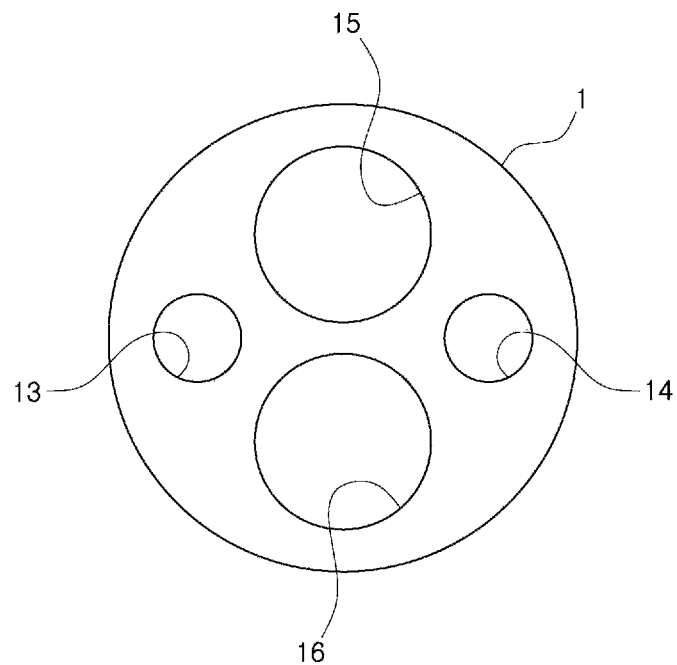
FIG. 4 is a cross sectional view of an example of the tube of FIG. 1.
Figure 5:
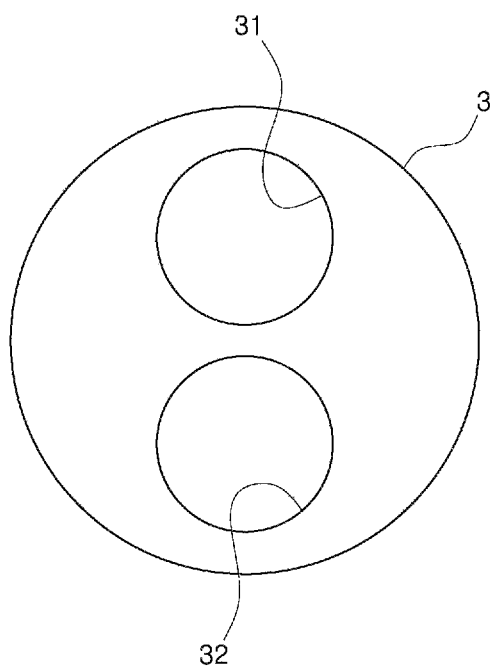
FIG. 5 is a cross sectional view of an example of the cap of FIG. 1.
Figure 6A:
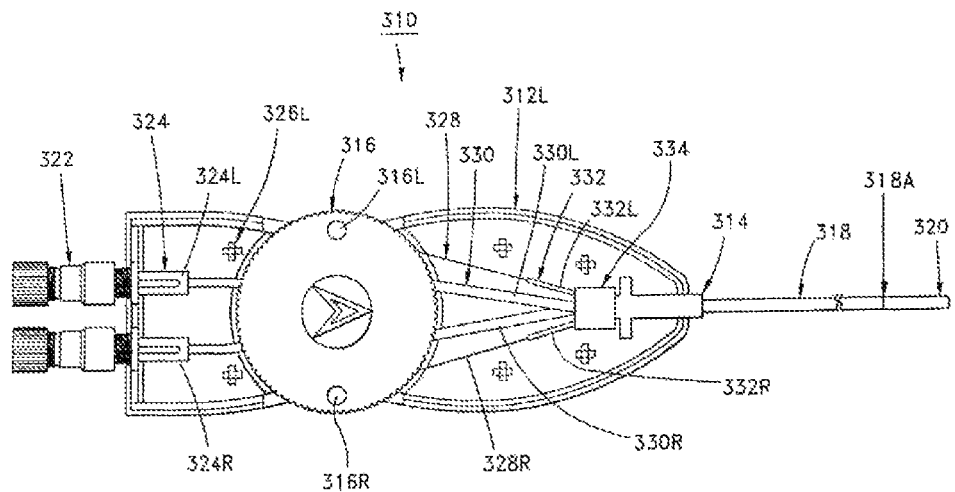
FIG. 6A is a top view of a related catheter.
Figure 6B:
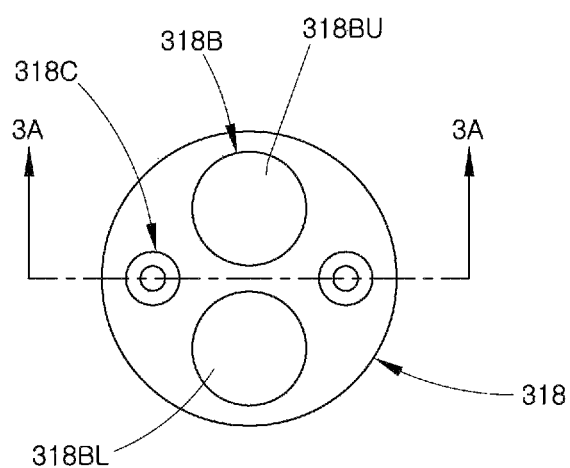
FIG. 6B is a cross sectional view of a lumen extrusion tip of the related catheter.
Figure 7:
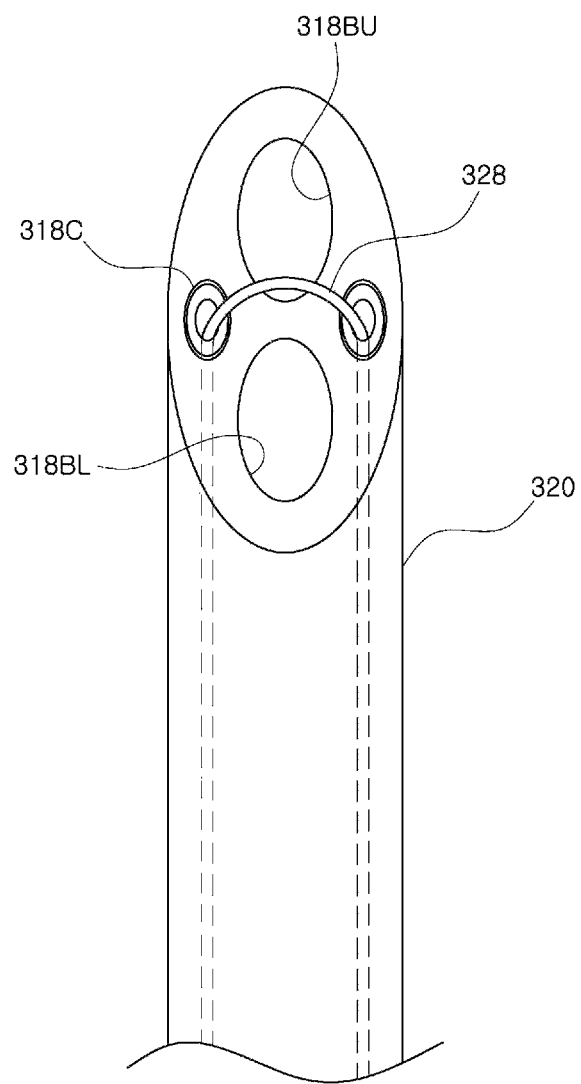
FIG. 7 illustrates an end of a catheter being deformed when tensile force is exerted on the wire of the catheter of FIG. 6.

As illustrated in FIG. 3, the wire 2 may be passed through, for example, two holes 13, 14 among the plurality of holes 13, 14, 15, 16 formed in the tube 1, with both ends thereof being fixed at the adjustment dial (not illustrated).

The cap 3 is engaged with an extrusion portion 21 of the wire 2 extruded from the two holes 13, 14 formed in the tube 1, in a manner of enclosing the extrusion portion 21 of the wire 2.

Meanwhile, in order to engage the cap 3 with the wire 2, for example, the wire 2 may be arranged with a mold for forming the cap 3, and then the extrusion portion 12 of the wire 2 may be finally fixed with the cap 3 by injection molding. Additionally, the cap 3 may be connected with one end of the tube 1, i.e., connected with one end of the second portion 12 of the tube 1 by bonding, or the like. For reference, the extrusion portion 21 of the wire 2 may have a U-shape. Further, the cap 3 is connected with the tube 1, with the holes 31, 32 thereof being in fluid with the holes 15, 16 of the tube 1, respectively.

Figure 2A:
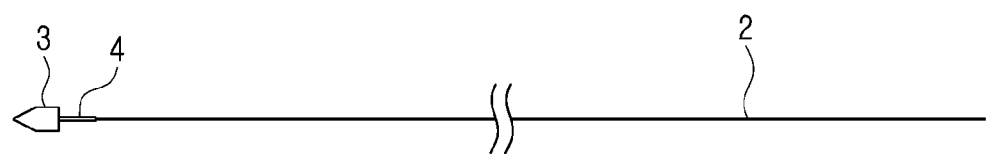
FIGS. 2A and 2B are respectively front view and top view illustrating a wire, a cap, and a pipe of the catheter of FIG. 1 in assembled state.
Figure 2B:
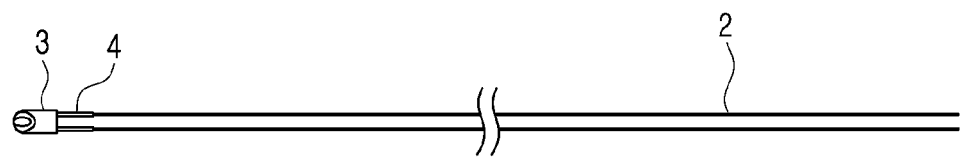

As illustrated in FIG. 2, the pipe 4 surrounding the wire 2 may be fixedly engaged with a lower side (right-side of the cap 3 based on FIG. 2B) of the cap 3 to prevent the wire 2 from sliding within the cap 3 when the tensile force is exerted on the wire 2. The pipe 4 may be engaged with the wire 2 by bonding. Further, the pipe 4 may be formed of a same metal material as the wire 2.

Meanwhile, in order to ensure that the end of the tube 1 is easily bent according to the rotation of the adjustment dial, it is important to ensure that the wire 2 is fixedly engaged with the end of the catheter and kept from relatively sliding at the end of the catheter. When the catheter is in actual use, under the tensile force repeatedly exerted to the wire in clockwise or counter-clockwise direction, the wire can be relatively slid with respect to the end of the catheter. The catheter according to the present disclosure prevents the above, because, first, the cap 3 and the wire 2 are engaged by injection molding so that the wire 2 is securely fixed to the cap 3, and second, a pair of pipes 4 are fixedly disposed at a lower side of the cap 3 to surround the wire 2. As a result, relative sliding of the wire 2 with respect to the cap 3 can be certainly prevented.

The catheter according to the present disclosure is fabricated such that, the wire 2 is disposed in a fashion illustrated in FIG. 3 and then an assembly of the cap 3 and the wire 2 is fabricated by injection molding, or the like.

Next, the pipes 4 are bonded to a lower side of the cap 3 to surround the wire 2.

Figure 1B:
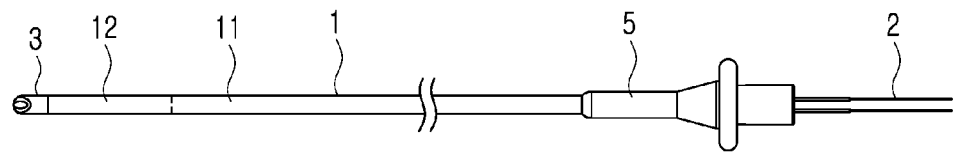

Next, the wire 2 is inserted in the tube 1 in the fashion illustrated in FIG. 1, and then the cap 3 and the tube 1 may be fabricated by, for example, bonding.

Figure 8:
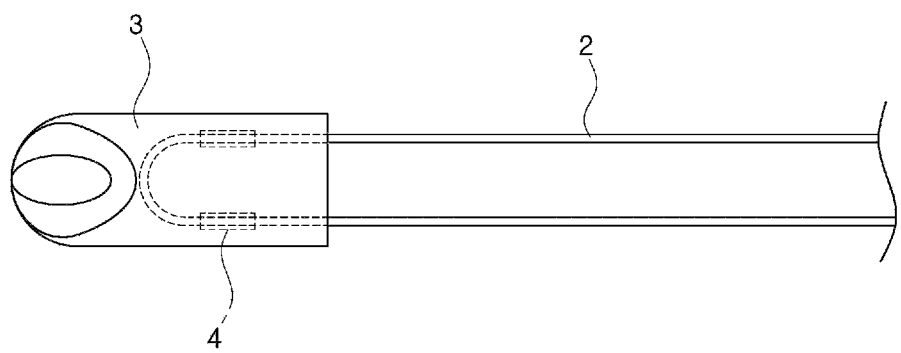
FIG. 8 illustrates a catheter according to another embodiment of the present disclosure.

Hereinbelow, a catheter according to another embodiment of the present disclosure will be described with reference to FIG. 8.

The elements or operations overlapped with the catheter according to the embodiment described above will not be redundantly described, while only the differences will be mainly described below.

In the catheter according to another embodiment of the present disclosure, a pair of pipes 4 surrounding the wire 2 are mounted within the cap 3. This may be achieved by first assembling the pipes 4 with the wire 2, then positioning the same in a mold to fabricate the cap 3, and then performing injection molding. An example of a method for assembling the pipes 4 with the wire 2 may include fitting the pipes 4 in the wire 2 and pressing the pipes 4 in such state to a fixed state.

In the catheter according to an embodiment of the present disclosure, during bonding of the pipes 4 to the lower side of the cap 3 to surround the wire 3, there may be a possibility that such bonding is incomplete so that the pipes 4 fail to securely grip the wire 3, in which case the wires 3 gradually move into the lower side of the cap 3 (as indicated by arrow 'A' in FIG. 3) and eventually separated out of the cap 3.

However, in the catheter according to another embodiment of the present disclosure, the pipes 4 are disposed within the cap 3 by injection molding, in which case the pipes 4 are practically immovable within the cap 3. Accordingly, it is possible to stably support the wire 3. Further, unlike the catheter according to the embodiment described above in which the pipes 4 support the cap 3 only on one surface (i.e., on surface contact) between the pipes 4 and the cap 3, in an embodiment in which the pipes 4 are disposed by injection molding within the cap 3, the supporting surface is increased in number to a plurality of surfaces, and as a result, the possibility of the wire 3 separating from the cap 3 can be fundamentally prevented.

An operation of a catheter according to an embodiment of the present disclosure will be described below.

In order to bend the tube 1 to a desired direction, the adjustment dial (not illustrated) with both ends of the wire 2 being fixed thereto are rotated clockwise or counterclockwise. Accordingly, an end of the tube 1 is bent to the desired direction due to difference in the bending rigidity between the first portion 11 and the second portion 12. At this time, since the rigid cap 3 of greater rigidity than the first portion 11 and the second portion 12 of the tube 1 is connected to the end of the tube 1, unlike the conventional catheter, the catheter according to the present disclosure does not suffer a problem of deformed cross section of the tube when the tensile force is exerted on the wire 2.

Accordingly, it is possible to inject medication (rinsing fluids) efficiently through the hole 1 of the tube 1 and the hole 31 of the cap 3, and efficiently insert or adjust an endoscope through the hole 16 of the tube 1 and the hole 32 of the cap 3.

Further, since the pipes 4 are fixedly engaged with a portion of the wire 2 that is adjacent to the cap 3, when the tensile force is exerted on the wire 2 to bend the end of the catheter to a desired direction, the pipes 4 fixedly engaged with the wire 2 are locked in the lower surface of the cap 3. Accordingly, a sliding motion of the wire 2 within the cap 3 relative to the cap 3 is prevented, which will thus enable effective bending of the end of the catheter.

Further, as an alternative, it is possible to stably support the wire 2 by disposing the pipes 4 within the cap 3 by injection molding, and thus basically preventing the pipes 4 from moving within the cap 3.

The foregoing exemplary embodiments and advantages are merely exemplary and are not to be construed as limiting the exemplary embodiments. The present teaching can be readily applied to other types of apparatuses. Also, the description of the exemplary embodiments of the present inventive concept is intended to be illustrative, and not to limit the scope of the claims.

INDUSTRIAL APPLICABILITY

The catheter according to the present invention can be inserted in a human body etc. and used for a variety of purposes such as injection of medication or rinsing fluids, and so on.

The invention claimed is:

1. A catheter, comprising:
 a tube comprising a first portion, a second portion connected to the first portion and having a less rigidity than the first portion, and a plurality of holes longitudinally penetrating the first portion and the second portion and being isolated from one another;
 a wire passing through two of the plurality of holes of the tube; and
 a cap being engaged with an extrusion portion of the wire extruded from the two holes of the tube in a manner of enclosing the extrusion of the wire, being connected to one end of the second portion of the tube, and having a greater rigidity than the first portion and the second portion of the tube,
 wherein pipes, fixedly engaged with the wire while surrounding the wire, are respectively fixed within the cap to prevent relative sliding of the wire within the cap with respect to the cap when tensile force is exerted on the wire.

2. The catheter of claim 1, wherein the pipes comprise two pipes.

3. A manufacturing method of the catheter according to claim 1, comprising:
 first assembling the pipes to the wire to prepare an assembly of the wire and the pipes; and
 disposing the assembly within a mold to fabricate the cap and then engaging the cap and the assembly by injection molding.

4. A manufacturing method of the catheter according to claim 2, comprising:
 first assembling the pipes to the wire to prepare an assembly of the wire and the pipes; and
 disposing the assembly within a mold to fabricate the cap and then engaging the cap and the assembly by injection molding.

5. The catheter of claim 1, wherein the wire is fixedly engaged with an inner surface of each of the pipes, and an outer surface of each of the pipes is fixedly disposed within the cap.

* * * * *